(12) United States Patent
Calhoun et al.

(10) Patent No.: US 7,767,222 B2
(45) Date of Patent: Aug. 3, 2010

(54) APPARATUS AND METHOD FOR PREVENTING ADHESIONS BETWEEN AN IMPLANT AND SURROUNDING TISSUES

(75) Inventors: Christopher J. Calhoun, San Diego, CA (US); Ralph E. Holmes, San Diego, CA (US); G. Bryan Cornwall, San Diego, CA (US)

(73) Assignee: MAST Biosurgery AG, Zurich (CH)

( * ) Notice: Subject to any disclaimer, the term of this patent is extended or adjusted under 35 U.S.C. 154(b) by 1054 days.

(21) Appl. No.: 10/632,014

(22) Filed: Jul. 31, 2003

(65) Prior Publication Data
US 2004/0115241 A1 Jun. 17, 2004

Related U.S. Application Data

(60) Provisional application No. 60/409,137, filed on Sep. 9, 2002, provisional application No. 60/399,813, filed on Jul. 31, 2002.

(51) Int. Cl.
*A61K 9/00* (2006.01)
*A61F 2/12* (2006.01)

(52) U.S. Cl. .......................................... 424/426; 623/8
(58) Field of Classification Search ................ 424/426, 424/450; 623/8
See application file for complete search history.

(56) References Cited

U.S. PATENT DOCUMENTS

| | | | |
|---|---|---|---|
| 3,636,956 A * | 1/1972 | Schneider | 606/224 |
| 3,874,986 A | 4/1975 | Browall et al. | |
| 4,464,320 A | 8/1984 | Chau et al. | |
| 4,603,695 A | 8/1986 | Ikada et al. | |
| 4,769,038 A | 9/1988 | Bendavid et al. | |
| 4,955,907 A * | 9/1990 | Ledergerber | 623/8 |
| 5,030,220 A | 7/1991 | Howland | |
| 5,047,054 A * | 9/1991 | Vijayan et al. | 623/23.6 |
| 5,227,412 A | 7/1993 | Hyon et al. | |
| 5,270,300 A | 12/1993 | Hunziker | |
| 5,380,329 A | 1/1995 | Elia et al. | |
| 5,412,068 A | 5/1995 | Tang et al. | |
| 5,437,672 A | 8/1995 | Alleyne | |
| 5,508,036 A * | 4/1996 | Bakker et al. | 424/424 |
| 5,525,646 A | 6/1996 | Lundgren et al. | |
| 5,609,629 A | 3/1997 | Fearnot et al. | |
| 5,626,861 A | 5/1997 | Laurenoin et al. | |
| 5,679,723 A | 10/1997 | Cooper et al. | |
| 5,686,090 A | 11/1997 | Schilder et al. | |
| 5,759,190 A | 6/1998 | Vibe-Hansen et al. | |
| 5,776,195 A | 7/1998 | Derycke | |
| 5,795,584 A | 8/1998 | Totakura et al. | |
| 5,797,946 A | 8/1998 | Chin | |
| 5,906,997 A | 5/1999 | Schwartz et al. | |
| 5,932,539 A | 8/1999 | Stupp et al. | |
| 6,005,162 A | 12/1999 | Constantz | |
| 6,034,140 A | 3/2000 | Schwartz et al. | |
| 6,113,640 A | 9/2000 | Tormala et al. | |
| 6,132,668 A | 10/2000 | Baars et al. | |
| 6,133,325 A | 10/2000 | Schwartz et al. | |
| 6,136,333 A | 10/2000 | Cohn et al. | |
| 6,153,252 A | 11/2000 | Hossainy et al. | |
| 6,211,217 B1 | 4/2001 | Spinale et al. | |
| 6,244,868 B1 | 6/2001 | Schappert | |
| 6,280,473 B1 | 8/2001 | Lemperle et al. | |
| 6,331,312 B1 | 12/2001 | Lee et al. | |
| 6,333,029 B1 | 12/2001 | Vyakarnam et al. | |
| 6,391,059 B1 | 5/2002 | Lemperle et al. | |
| 6,451,373 B1 * | 9/2002 | Hossainy et al. | 427/2.25 |
| 6,530,956 B1 | 3/2003 | Mansmann | |
| 6,531,146 B2 | 3/2003 | Calhoun et al. | |
| 6,596,267 B1 | 7/2003 | Hubbell et al. | |
| 6,673,362 B2 | 1/2004 | Calhoun et al. | |
| 6,719,795 B1 | 4/2004 | Cornwall et al. | |
| 7,074,239 B1 | 7/2006 | Cornwall et al. | |
| 7,537,782 B2 | 5/2009 | Calhoun et al. | |
| 2001/0004693 A1 | 6/2001 | Burkhead et al. | |
| 2001/0056303 A1 | 12/2001 | Caneiro et al. | |

(Continued)

FOREIGN PATENT DOCUMENTS

EP 0224460 A2 6/1987

(Continued)

OTHER PUBLICATIONS

Arm et al., Sustained Release Compositions for Delivery of Growth Factors, Oct. 28, 1993, International Application Published Under the PCT, WO 93/20859.*

(Continued)

*Primary Examiner*—Johann R Richter
*Assistant Examiner*—Ali Soroush
(74) *Attorney, Agent, or Firm*—Stout, Uxa, Buyan & Mullins, LLP

(57) ABSTRACT

An anti-adhesion membrane is placed onto an implant introduced into a surgical site of a patient to prevent post-surgical adhesions between the implant and surrounding tissue. The implant may comprise either biological material, whcu as a transplanted organ, or non-biological material such as a medical device. The membrane may be applied in a variety of ways. In one example, a membrane according to the present invention is shrink-wrapped around a pace-maker. In another example, a breast implant is spray-coated or dipped with the membrane material.

32 Claims, 2 Drawing Sheets

U.S. PATENT DOCUMENTS

| | | | |
|---|---|---|---|
| 2002/0001609 A1* | 1/2002 | Calhoun et al. | 424/426 |
| 2002/0173213 A1 | 11/2002 | Chu et al. | |
| 2003/0059463 A1* | 3/2003 | Lahtinen | 424/450 |
| 2003/0185874 A1 | 10/2003 | Calhoun et al. | |
| 2004/0018175 A1 | 1/2004 | Dimitrijevich | |
| 2004/0030304 A1 | 2/2004 | Hunt et al. | |
| 2005/0074495 A1 | 4/2005 | Schwartz et al. | |
| 2005/0175665 A1 | 8/2005 | Hunter et al. | |

FOREIGN PATENT DOCUMENTS

| | | |
|---|---|---|
| EP | 1384450 A1 | 1/2004 |
| JP | 7116241 A | 5/1995 |
| JP | 2000503555 A | 3/2000 |
| JP | 2000189509 A | 7/2000 |
| JP | 2000265333 A | 9/2000 |
| JP | 2003103429 A | 4/2003 |
| JP | 2007504227 A | 3/2007 |
| JP | 200833718 A | 2/2008 |
| JP | 2008300481 A | 12/2008 |
| WO | 9013302 | 11/1990 |
| WO | 9317635 A1 | 9/1993 |
| WO | 9320859 | 10/1993 |
| WO | 9320859 A1 | 10/1993 |
| WO | 9951163 | 10/1999 |
| WO | 0015270 A1 | 3/2000 |
| WO | 0015273 A1 | 3/2000 |
| WO | 0062707 | 10/2000 |
| WO | 0167987 | 9/2001 |
| WO | 0167987 A1 | 9/2001 |

OTHER PUBLICATIONS

Arm et al., "Sustained Release Compositions for delivery of Groth Factors", Oct. 28, 1993, International Application Published Under the PCT, WO 93/20859. (Previously submitted).*

Massie et al., "Antifbrotics gels versus a barrier sheet in the prevention of epidural fibrosis postlaminectomy.", 2001, Presented at 16th Annual Meeting of North American Spine Society. (See IDS Submission).*

Welch et al., "Use of polylactide resorbable film as an adhesion barrier", Nov. 2002, Journal of Neurosurgery: Spine, vol. 97, pp. 413-422.*

International Search Report, Jan. 11, 2005.
International Search Report, Jun. 6, 2001, PCT/US01/07989.
International Search Report, Jan. 11, 2005, PCT/US03/23919.
International Search Report, Jan. 11, 2005, PCT/US03/24824.
International Search Report, Mar. 2, 2006, PCT/US05/28834.
International Serch Report, Mar. 2, 2006, PCT/US05/28834.
Casey K. Lee et al. "Prevention of Postlaminectomy Scar Formation" Spine, vol. 9, No. 3, 1984, p. 305-312.
Maglio G et al. "Compatibilized poly (Epsilon-Caprolactone)/Poly(L-Lactide) Blends for Biomidical Uses" Macromol, Rapid Commun 20 No. 4, p. 236-238 (1999).
Dieter Bendix "Chemical synthesis of polylactide and its copolymers for medical applications" Polymer Degradation and Stability 59 (1998) p. 129-135.
Gates, Kimberly "Controlled Drug Delivery Using Bioerodible Polymeric Systems for the Treatment of Periodontitis" Graduate Department of Pharmaceutical Sciences, University of Toronto (1999), printed pp. 1-173, especially p. 56.
Supplementary European Search Report from application No. EP 03772191, mailed Aug. 31, 2009.
Supplementary European Search Report from application No. EP 05786506, mailed Sep. 10, 2009.
International Search Report and Written Opinion from application No. PCT/US09/49728, mailed Aug. 19, 2009.
International Search Report and Written Opinion, PCT/IB2008/003797, mailed Jan. 12, 2010.
Dieter Bendix, Chemical Synthesis of Polylactide and its Copolymers for Medical Applications, 129-135, Published 1988.
Casey K. Lee and Harold Alexander, Prevention of Postlaminectomy Scar Formation, 305-312, Published Apr. 1984.

* cited by examiner

APPARATUS AND METHOD FOR PREVENTING ADHESIONS BETWEEN AN IMPLANT AND SURROUNDING TISSUES

CROSS-REFERENCE TO RELATED APPLICATIONS

This application claims the benefit of priority of Prov. App. 60/409,137, filed Sep. 9, 2002, and of Prov. App. 60/399,813, filed Jul. 31, 2002. The foregoing applications are commonly assigned and the contents of all are expressly incorporated herein by reference.

This application is related to application Ser. No. 10/631, 980 (now U.S. Pat. No. 7,592,017), which is a continuation-in-part of application Ser. No. 10/385,399 (now U.S. Pat. No. 6,673,362), which is a continuation of application Ser. No. 09/805,411 (now U.S. Pat. No. 6,531,146).

BACKGROUND OF THE INVENTION

1. Field of the Invention

This invention relates generally to medical devices and, more particularly, to methods and apparatus for reducing post-surgical adhesions between living tissues and an implant introduced into a surgical site of a patient;

2. Description or Related Art

A major clinical problem relating to surgical procedures or inflammatory diseases can be unwanted tissue growth, or adhesion, which can occur during the initial phases of the healing process after surgery or disease. Another problem can be foreign body reactions in response to medical devices or implants introduced into a surgical site. Still another problem can be leakage, migration or diffusion of substances, for instance fluids, from an implant into surrounding tissues.

One approach to the problem of adhesion has been the use of bioresorbable barrier materials, in the form of gels, coatings, fabrics, foams, films, and the like, that are placed between a healing post-surgical site and adjacent surrounding tissue. Examples of such barrier materials can be found in U.S. Pat. No. 5,412,068 to Tang et al., U.S. Pat. No. 5,795,584 to Totakura, U.S. Pat. Nos. 6,034,140 and 6,133,325 to Schwartz et al., and U.S. Pat. No. 6,136,333 to Cohn et al., all of which are expressly incorporated herein by reference.

More specifically, the patent to Tang et al. discloses films and other bioresorbable medical devices formed from polycarbonate fibers. The patent to Totakura discloses surgical adhesion barriers comprising copolymers and/or block copolymers derived from trimethylene carbonate. The patents to Schwartz et al. disclose anti-adhesion membranes made of carboxyl-containing polysaccharides and polyethers. The patent to Cohn et al. discloses polymeric anti-adhesion compositions comprising poly(ester)/poly(oxyalkylene) ABA triblocks or AB diblocks. Similarly, the problem of foreign body reactions has been addressed by applying biocompatible polymeric coatings to medical devices, such as, for instance, stents. An exemplary method for coating a stent is disclosed in U.S. Pat. No. 6,153,252 to Hossainy et al., also expressly incorporated herein by reference.

Unfortunately, the coatings and other barriers discussed above have met with only limited success. For instance, some of the prior art barrier materials may be resorbed into the body too quickly, yielding undesirable drops in local pH levels, which may cause or exacerbate such problems as local inflammation, discomfort and/or foreign antibody responses. Other materials may take too long to resorb, may be insufficiently malleable, or may require complex chemical formulations and/or reactions which can increase the cost of manufacturing.

SUMMARY OF THE INVENTION

New applications have been discovered for anti-adhesion membrane materials. Specifically, it has been discovered that, in addition to their use as barriers between adjacent living tissues, anti-adhesion membranes disclosed herein can be suitable for placement onto implants introduced into a surgical site of a patient, in order to prevent undesired reactions between the implant and surrounding tissues. The implant may be either a biological implant such as a transplanted organ, or a non-biological implant such as a medical device implant. Among the devices to which the principles of the invention can be applied are bone graft substitutes, bone cement, tissue glues and adhesives, bone fixation members (plates, mesh, screws and rods), prostheses, tissue augmentation devices (such as breast implants, penile implants and collagen), pacemakers, defibrillators, eye spheres, sutures, tacks, staples, cochlear implants, pumps, artificial organs, non-resorbable sheets and membranes, bone growth stimulators, neurological stimulators, dental implants, guided tissue and guided bone regeneration membranes, eye lid weights and tympanostomy tubes. The type of membrane material in any particular application is determined depending on the application and the characteristics of the surgical site to which the membrane is being applied.

Of particular interest are the resorbable micro-membranes, or films, that are disclosed in U.S. patent application Ser. No. 09/805,411 filed Mar. 12, 2001, and expressly incorporated herein by reference. Specifically, the aforementioned application discloses scar tissue-reduction barrier membranes that are constructed entirely of resorbable polymers, and are engineered to be absorbed into the body relatively slowly over time in order, for example, to reduce potential negative side effects. In a preferred embodiment of that invention, the membrane material is selected from the group consisting of lactide polymers (e.g., copolymers) of two or more lactides. It has now been found that these polylactide membranes have additional use as protective barriers for use on foreign bodies such as implants.

Also of interest are the membrane-forming techniques disclosed in U.S. Provisional Patent Application Ser. No. 60/399,792, filed Jul. 31, 2002, and U.S. Provisional Patent Application Ser. No. 60/408,393, filed Sep. 4, 2002 both of which are expressly incorporated herein by reference. Membranes formed by these techniques have been found to be particularly effective for the use on foreign body implants as disclosed herein.

In a method according to the present invention, an anti-adhesion membrane is applied onto an implant before the body of the implant is introduced into a surgical site of a patient. The implant may comprise either biological material, such as a transplanted organ, or non-biological material such as a medical device implant. The membrane may be applied to the implant in a variety of ways. In one example, a membrane according to the present invention is shrink-wrapped around an implant, such as a pace-maker. In another example, an implant, such as a breast implant, is spray-coated with the membrane material disclosed herein.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

DESCRIPTION OF THE PRESENTLY PREFERRED EMBODIMENTS

Figure 1:
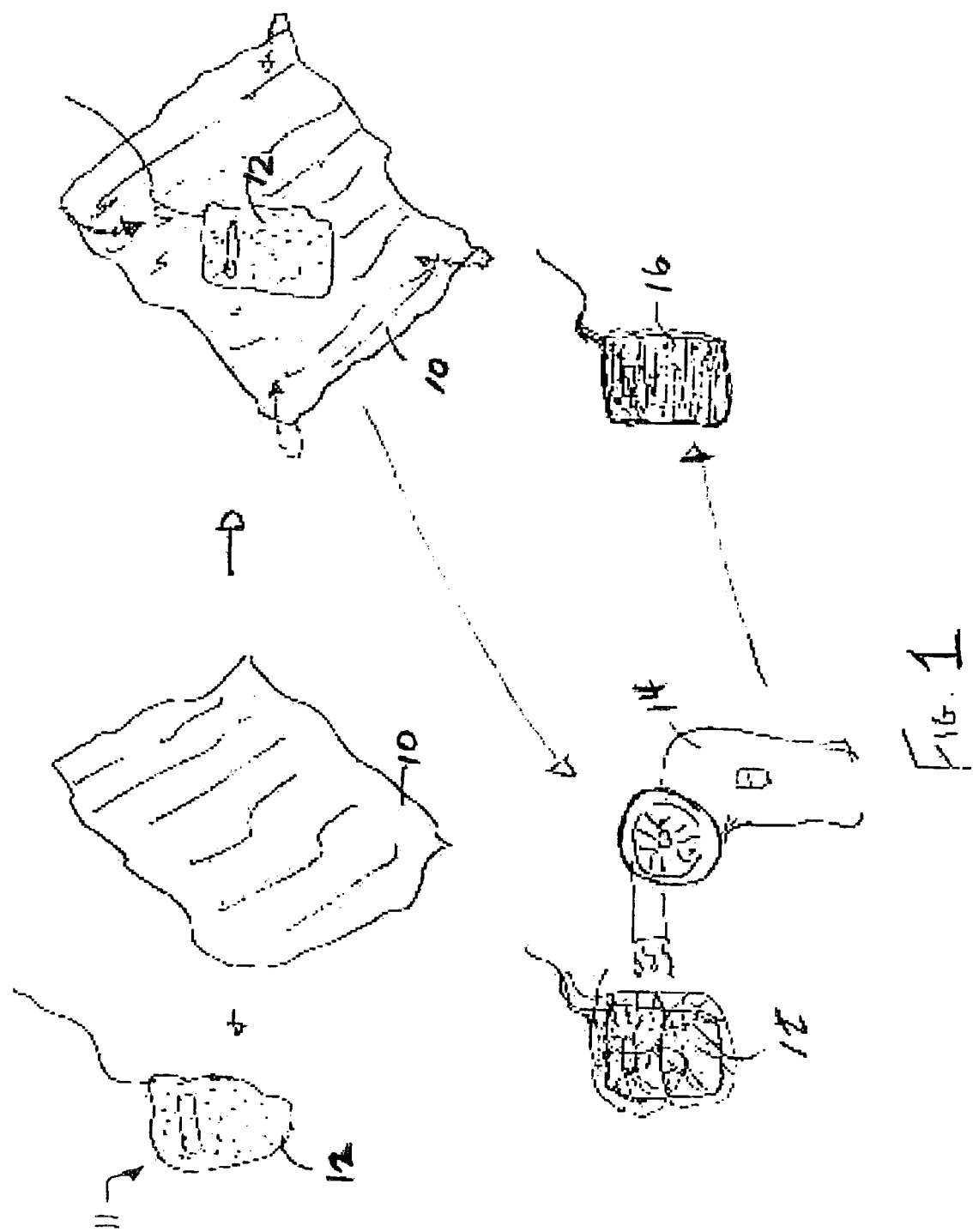
FIG. 1 is a schematic illustration showing a method of coating a pace-maker according to one embodiment of the invention.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

The present invention is directed to a method of reducing post-surgical adhesions between an implant and surrounding tissues at a surgical site, comprising a step of applying and/or forming an anti-adhesion membrane on and around the implant. The apparatus, which comprises the implant and the anti-adhesion membrane, may then be placed in a patient at a surgical site.

Membranes of the present invention may be constructed from various biodegradable materials, such as resorbable polymers. For example, the membrane material applied to or formed on the implants comprises lactide polymers, such as copolymers of two or more lactide monomers. In one embodiment, the membrane material is preferably selected from the group consisting of lactide polymers (e.g., copolymers) of two or more monomers. In accordance with one embodiment of the present invention, non-limiting polymers which may be used to form membranes of the present invention include polymers (e.g., copolymers) of lactide (L, D, DL, or combinations thereof), glycolide, trimethylene carbonate, caprolactone and/or physical and chemical combinations thereof. In one embodiment, the membranes comprise a polylactide, which can be a copolymer of L-lactide and D,L-lactide. For example, the copolymer can comprise about 60-80% of L-lactide and about 20-40% of D,L-lactide, and in a preferred embodiment the copolymer comprises poly (L-lactide-co-D,L-lactide) 70:30 Resomer LR708 manufactured and supplied from Boehringer Ingelheim KG of Germany. Membranes constructed from this material have been found to retard or prevent tissue adhesions, reduce scarring and/or inflammation, and to be resorbable within 24 months or less of implantation into the mammalian body.

In one embodiment, the membranes are formed by polymers (e.g., homo and/or copolymers) derived from one or more cyclic esters, such as lactide (i.e., L, D, DL, or combinations thereof), epsilon-caprolactone and glycolide. For instance, the membranes in one embodiment can comprise about 1 to 99% epsilon-caprolactone, or in another embodiment can comprise 20 to 40% epsilon-caprolactone. In one example, a membrane comprises 65:35 poly (L-lactide-co-epsilon-caprolactone). In other embodiments, butyrolactone, valerolactone, or dimethyl propiolactone can be used with or as a substitute for epsilon-caprolactone. In another embodiment, the membranes can comprise a copolymer including lactide and glycolide which is resorbed into the body more rapidly than the above-mentioned poly (L-lactide-co-D,L-lactide).

The anti-adhesion membrane of the present invention may be applied to a wide variety of foreign bodies including, but not limited to, grafting material, transplanted organs and medical devices, including medical devices which may be surrounded by living tissue including, but not limited to, fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage. The grafting material may comprise autograft material, xenograft material, allograft material, and combinations thereof. Examples of suitable grafting material includes veins, arteries, heart valves, skin, dermis, epidermis, nerves, tendons, ligaments, bone, bone marrow, blood, white blood cells, red blood cells, gonadocytes, embryos, cells, adipose, fat, muscle, cartilage, fascia, membranes, pericardium, plura, periostium, peritoneum, and dura. Implants may include a transplanted organ, such as kidneys, hearts, eyes, and livers, among other things.

Other implants comprise non-biological materials, such as medical devices. Examples of suitable non-biological implants include, but are not limited to, bone graft substitutes, bone cement, tissue glues and adhesives, bone fixation members, defibrillators, eye spheres, sutures, staples, cochlear implants, pumps, artificial organs, non-resorbable membranes, bone growth stimulators, neurological stimulators, dental implants, guided tissue and guided bone regeneration membranes, eyelid weights, and tympanostomy tubes. Other medical devices may include prosthetics, such as a fluid filled prosthesis. One example of a fluid filled prosthesis is a breast implant, such as a saline or silicone breast implant. In addition, medical devices may include electronic instruments, such as a pacemaker.

The membrane may be formed or applied on or over the implant or device using any of a number of techniques including, but not limited to, wrapping, interweaving, blanketing, draping, taping, adjacent placement, juxtaposed positioning, and sandwiching.

Figure 2:
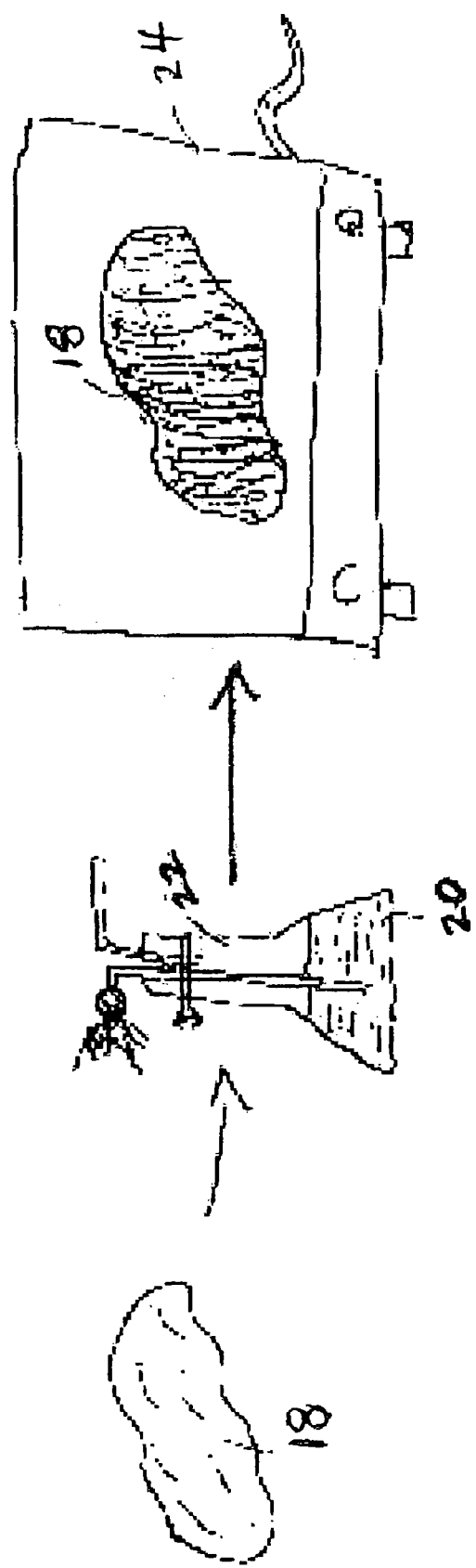
FIG. 2 is a schematic illustration showing a method of coating a breast implant according to another embodiment of the invention.

In a first embodiment of the invention, the anti-adhesion material is pre-formed as a membrane before application onto the implant. In a second embodiment of the invention, the material is applied as a coating which dries to form a membrane or barrier around the implant. The coated membrane may be effective as a protective layer around the implant, and/or may be effective as a resorbable barrier, as disclosed herein. One method of applying a pre-formed membrane is shown in FIG. 1. A method of forming a membrane by coating and drying is illustrated in FIG. 2. The material used to form the membranes in both figures can comprise, for example, poly (L-lactide-co-D,L-lactide). It is understood, however, that other bioresorbable polymers having anti-adhesion properties may be used in modified embodiments. In other modified embodiments, even nonresorbable polymers or polymers without anti-adhesion properties may be used, depending on the application of the membrane. For example, the membrane or barrier may include one or more portions that comprise a resorbable polymer or polymers, and one or more portions that comprise nonresorbable polymers.

FIG. 1 shows a method of applying a pre-formed membrane 10 to a medical device 11 such as a pacemaker 12. The pre-formed membrane 10 is preferably a non-porous film formed of a single layer of polylactide material adapted to maintain a smooth-faced barrier between an implant and surrounding tissues. More preferably, the material in its final form has viscosity property, such as an inherent viscosity, in the range of about 0.20 to about 10.00 g/dL at 25° C. in chloroform. For many applications, the viscosity property of the disclosed membranes is optimally in the range of about 1.00 to about 3.00 g/dL. In one embodiment, the viscosity property is greater than 1 g/dL, and preferably greater than 2 g/dL, and more preferably about 3 g/dL. It is also highly preferable that the thickness of the membrane be less than about 300 microns, and more preferably, in the range of about 10 to about 100 microns. In one preferred embodiment, the thickness is in the range of about 10 to about 50 microns. This thickness should be uniform in the axial and transaxial directions, except at the outermost edges of the membrane 10, where the thickness can be 2 to 4 times thicker than the rest of the membrane. The thicker edges can provide the membrane with added attachment strength and reduce the risk of damage in for example attachment applications.

It is recommended that the membrane 10 be pre-formed using the extrusion and stretching techniques disclosed in U.S. Provisional Patent Application Ser. No. 60/399,792, and U.S. Provisional Patent Application Ser. No. 60/408,393. However, other standard film-forming processes may be used in modified embodiments. For instance, compression molding may be used, or any appropriate technique described in, for instance, the Encyclopedia of Polymer Science and Engineering, Vol. 12, pp. 204-210 (1988), the contents of which are incorporated herein by reference. However, due to the extreme thinness of the membrane 10, certain techniques, such as injection molding, may not be suitable, and may not provide sufficient performance. By using certain fabrication techniques, multiple layers of the polymeric materials may be formed in one membrane. Multilayer membranes may provide improved benefits and advantages especially when more than one resorbable material is used, such as a first resorbable material that degrades at a first rate, and a second resorbable material that degrades at a second rate.

After formation, the membrane 10 is placed on or under the pacemaker 12, and wrapped around the pacemaker 12 to substantially encase the pacemaker. As illustrated in FIG. 1, the pacemaker is completely encased. For other implants, including pacemakers, the membrane 10 may be wrapped around the majority of the implant so that only a minor portion of the implant is in direct contact with a biological environment of a human or animal patient in which the implant is placed. As shown in FIG. 1, an air blower 14 or other heating device is then used to increase the temperature of the membrane 10, which may be supported on a suitable frame or holder (not shown), to a value above glass transition temperature. In the case of the preferred polylactide material, the glass transition temperature is about 55° C. to about 60° C. While in the glass transition state, the membrane 10 shrinks in a predictable manner, depending on the process used to manufacture the membrane. For instance, a membrane which has been monoaxially extruded according to the process disclosed in the aforementioned co-pending U.S. patent application, may shrink by a factor of about 3 along one axis (in a preferred embodiment, the longitudinal axis), and by a factor of about 10-15% on a transverse axis. A membrane which has been biaxially extruded may, in one embodiment, shrink approximately equally along both axes. After cooling back below glass transition temperature, the membrane 10 hardens or is set in its new, wrapped configuration 16. The wrapped configuration may include the membrane 10 wrapped tightly around the implant. In certain embodiments, substantially all of the exposed surfaces of the implant are covered by the membrane. In further embodiments, the membrane is in direct contact with the surfaces of the implant. In other embodiments, the membrane may be wrapped around the implant so that the membrane is not in contact with the implant surfaces, but substantially surrounds the implant. For example, the membrane may be configured as a bag that can be wrapped around the implant with a gas or liquid filled space between the membrane and the implant. It is not believed that adhesives or other fixation structures or methods are needed to maintain the membrane 10 in its wrapped configuration. However, it is within the scope of the invention to apply molding to the wrapped implant, such as pacemaker 12, as it is heated and cooled, or to apply cement or other adhesives to the corners of the membrane as an added step.

Heat-shrinking may be effective in applications where for example a device or other implant is to be implanted into a surgical site of a patient, but not necessarily attached to any anatomical structure. In applications where the implanted device or implant is attached to an anatomical structure or tissue, it may be preferable to mechanically secure a pre-formed membrane to both the device or implant body and the surrounding structure or tissue. Among the techniques that can be employed are wrapping, interweaving, blanketing, draping, taping, adjacent placement, juxtaposed positioning and sandwiching of the membrane relative to the implant and the surrounding tissues or structure. Sutures or staples, for example, may also be used to attach a pre-formed membrane to surrounding muscle. As another example, a pre-formed membrane may be secured to bone using resorbable bone screws or tacks. In other cases, tucking or folding a membrane into anatomical crevices may be sufficient to fix its position. An adhesive such as a fibrin sealant or a resorbable cyanoacrylate adhesive may further be utilized to secure the pre-formed membranes, alone or in combination with any of the other means of attachment discussed above. Alternatively, a pre-formed membrane can be heat bonded, such as with a bipolar electro-cautery device, ultrasonically welded, or similarly sealed directly to the surrounding or adjacent structure.

In certain applications, for instance in cases where the implant to be implanted is bulky or irregularly shaped, it may be more practical to coat the implant than to apply a pre-formed membrane. For example, FIG. 2 shows a method of spray-coating a breast implant 18, which can be a saline-type implant in a silicone casing.

Preferably, a coating solution 20 is created by dissolving a bioresorbable polymer such as the poly(L-lactide-co-D,L-lactide) material described above in a suitable solvent. The solvent can be selected from the group comprising ethyl acetate, acetonitrile, acetone, methyl ethyl ketone (MEK), tetrahydrofuran (THF), methyl pyrole, and any combination of two or more of the above. In one embodiment of the invention, the solution 20 has a concentration of about 0.1 to about 5.0% by weight of the bioresorbable polymer. The solution 20 is placed in an appropriate sprayer 22 such as an ultrasonic spray unit, and sprayed as a fine mist over the surface of the implant 18. The solution may be sprayed using any conventional propellant. For example, the solution may be sprayed using a pump, or aerosol based spraying devices. The spraying may be performed under atmospheric conditions. After spraying, the implant 18 is dried, preferably air-dried for about 1 to 5 hours, to remove 80 to 90% of the solvent, and may then be placed in a vacuum oven 24 having a pressure of about $1\times10^{-2}$ mm Hg at, for instance, around 55° C. or less to remove as much of the remaining solvent as possible. In the case of organic solvents, in particular, it is important that minimal solvents remain, and preferably no solvents at all.

After the initial coating has been applied, one or more full or partial additional coatings may be added if necessary. The coating or coatings need not be uniform in thickness, but the final thickness at the thinnest section should be no less than about 10 microns. Preferably the final thickness at substantially all sections is in the range of about 10 to about 300 microns and, more preferably, in the range of 10 to about 50 microns. As discussed herein, providing multiple coatings with varying thicknesses may facilitate selective control of resorption rates of the barrier membranes.

The above-described embodiments have been provided by way of example, and the present invention is not limited to these examples. While the foregoing is a description of the preferred embodiments of the invention, various alternatives, modifications, and equivalents may be used. Moreover, it will be apparent that certain other modifications may be practiced within the scope of the appended claims.

What is claimed is:

1. A method of using a resorbable polymer base material in combination with an implant for attenuating adhesions between the implant and surrounding tissue following a surgical procedure in a human patient, the method comprising: providing a nonporous, resorbable polymer base material; heat-shrinking the resorbable polymer base material in a form of a resorbable thin membrane around the implant to thereby cover surfaces of the implant, wherein the resorbable thin membrane comprises a resorbable polymer consisting essentially of: a lactide polymer; or a copolymer of two or more cyclic esters; applying the implant and the resorbable thin membrane to a human patient in a region, which is susceptible to adhesions as a consequence of the surgical procedure; and attenuating an occurrence of adhesion between the implant and surrounding tissue at the region within the human patient by way of the presence of the resorbable thin membrane positioned at the region within the patient.

2. The method according to claim 1, wherein:
the resorbable thin membrane comprises a substantially planar membrane of resorbable polymer base material having a first substantially smooth side and a second substantially smooth side, the substantially planar membrane of resorbable polymer base material having a substantially uniform composition;
the substantially planar membrane of resorbable polymer base material comprises a single layer of resorbable polymer base material;
the substantially uniform thickness is measured between the first substantially smooth side and the second substantially smooth side, and is between about 10 microns and about 100 microns;
the resorbable thin membrane comprises an edge which is 2 to 4 times thicker than the substantially uniform thickness; and
the single layer of resorbable polymer base material is adapted to maintain a smooth-surfaced barrier between the implant and surrounding tissue, and is adapted to be resorbed into a mammalian body within a period of less than approximately 24 months from an initial implantation of the implant into the patient.

3. The method according to claim 1, wherein:
an edge of the resorbable thin membrane is 2-4 times thicker than the substantially uniform thickness;
the resorbable thin membrane comprises a layer of polymer base material; and
the polymer base material comprises about 60-80% of L-lactide and about 20-40% of D,L-lactide.

4. The method according to claim 1, wherein an edge of the resorbable thin membrane is 2-4 times thicker than the substantially uniform thickness, and the resorbable thin membrane is in contact with the surfaces of the implant when it is applied to the implant.

5. The method according to claim 1, wherein:
an edge of the resorbable thin membrane is 2-4 times thicker than the substantially uniform thickness; and
the step of applying the thin membrane onto the implant comprises a technique selected from the group consisting of wrapping, interweaving, blanketing, draping, taping, adjacent placement, juxtaposed positioning and sandwiching of the membrane onto the implant.

6. The method according to claim 1, wherein: an edge of the resorbable thin membrane is 2-4 times thicker than the substantially uniform thickness.

7. The method according to claim 1, wherein the step of applying the thin membrane onto the implant comprises:
dissolving a polymer material in a solvent to form a solution; and
coating the implant with the solution.

8. The method according to claim 7, wherein:
the polymer material is selected from the group consisting essentially of a lactide polymer and a copolymer of two or more lactides; and
the solvent is selected from the group comprising ethyl acetate, acetonitrile, acetone, methyl ethyl ketone, tetrahydrofuran, methyl pyrole, and any combination thereof.

9. The method according to claim 8, wherein the solution comprises a concentration in the range of about 0.1 to about 5.0% of the polymer.

10. The method according to claim 7, further comprising a step of drying the coated implant before placement into a surgical site.

11. The method according to claim 10, wherein the step of drying comprises drying the coated implant in a vacuum oven.

12. The method according to claim 11, further comprising the step of air drying the coated implant before placement in the vacuum oven.

13. The method according to claim 7, wherein the step of coating the implant comprises spraying the implant with the solution.

14. The method according to claim 1, wherein an edge of the resorbable thin membrane is 2-4 times thicker than the substantially uniform thickness, and the implant comprises biological material.

15. The method according to claim 14, wherein the biological material comprises grafting material.

16. The method according to claim 15, wherein the grafting material is selected from the group consisting of autograft material, xenograft material, allograft material, and combinations thereof.

17. The method according to claim 15, wherein the grafting material is selected from the group consisting of veins, arteries, heart valves, skin, dermis, epidermis, nerves, tendons, ligaments, bone, bone marrow, blood, white blood cells, red blood cells, gonadocytes, embryos, cells, adipose, fat, muscle, cartilage, fascia, membranes, pericardium, plura, periostium, peritoneum and dura.

18. The method according to claim 15, wherein the surrounding tissue is selected from the group comprising fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage.

19. The method according to claim 1, wherein an edge of the resorbable thin membrane is 2-4 times thicker than the substantially uniform thickness, and the implant comprises a transplanted organ.

20. The method according to claim 19, wherein the surrounding tissue is selected from the group comprising fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage.

21. The method according to claim 1, wherein an edge of the resorbable thin membrane is 2-4 times thicker than the substantially uniform thickness, and the implant comprises non-biological material.

22. The method according to claim 21, wherein the implant comprises a medical device.

23. The method according to claim 22, wherein the medical device is selected from the group consisting of bone graft substitutes, bone cement, tissue glues and adhesives, bone fixation members, defibrillators, eye spheres, sutures, staples, cochlear implants, pumps, artificial organs, non-resorbable membranes, bone growth stimulators, neurological stimulators, dental implants, guided tissue and guided bone regeneration membranes, eye lid weights and tympanostomy tubes.

24. The method according to claim 22, wherein the medical device comprises a fluid-filled prosthesis.

25. The method according to claim 23, wherein the surrounding tissue is selected from the group comprising fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage.

26. The method according to claim 24, wherein the surrounding tissue is selected from the group comprising fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage.

27. The method according to claim 24, wherein the fluid-filled prosthesis comprises a breast implant.

28. The method according to claim 27, wherein the breast implant comprises a saline implant contained within a silicone casing.

29. The method according to claim 22, wherein the implant comprises a pacemaker.

30. The method according to claim 1, wherein the edge is 2-4 times thicker than the substantially uniform thickness, and the implant comprises grafting material selected from the group consisting of autograft material, xenograft material, allograft material, and combinations thereof.

31. The method according to claim 30, wherein the grafting material is selected from the group consisting of veins, arteries, heart valves, skin, dermis, epidermis, nerves, tendons, ligaments, bone, bone marrow, blood, white blood cells, red blood cells, gonadocytes, embryos, cells, adipose, fat, muscle, cartilage, fascia, membranes, pericardium, plura, periostium, peritoneum and dura.

32. The method according to claim 1, wherein the edge is 2-4 times thicker than the substantially uniform thickness, and the surrounding tissue is selected from the group comprising fascia, soft tissues, muscle, organs, fat, adipose, membranes, pericardium, plura, periostium, peritoneum, dura, bowels, intestines, ovaries, veins, arteries, epidermis, tendons, ligaments, nerves, bone and cartilage.

* * * * *